United States Patent [19]

Bennett

[11] Patent Number: 5,378,686
[45] Date of Patent: Jan. 3, 1995

[54] THERAPEUTIC TREATMENT OF FIBROMYALGIA

[75] Inventor: Robert M. Bennett, Portland, Oreg.

[73] Assignee: Research Corporation Technologies, Inc., Tucson, Ariz.

[21] Appl. No.: 947,792

[22] Filed: Sep. 21, 1992

[51] Int. Cl.⁶ .............................................. A61K 37/36
[52] U.S. Cl. ........................................ 514/12; 530/399
[58] Field of Search ........................... 514/12; 530/399

[56] References Cited

U.S. PATENT DOCUMENTS 4,816,439  3/1989  Jorgensen .............................. 514/12

OTHER PUBLICATIONS

Bennett et al., "Low Somatomedin-C levels in Fibromyalgia" abstract, Arthritis Rheum 34 (9 Suppl.), p. 5188 (1991).
Astrom, C. et al., "Sleep in Acromegaly before & after treatment . . . ", Neuroendocrinology, vol. 53 (4), pp. 328–331 (1991).
Bennett, *J. of Rheumatology*, 16:185–191 (1989).
Bennett et al., *Arthritis and Rheumatism*, 35:1113–1116 (1992).

*Primary Examiner*—Michael G. Wityshyn
*Assistant Examiner*—C. Sayala
*Attorney, Agent, or Firm*—Dickstein, Shapiro & Morin

[57] ABSTRACT

Disclosed is a therapeutic regime for treating patients with fibromyalgia (FM) and other syndromes characterized by non-restorative sleep and musculoskeletal pain. Supplemental growth hormone (GH) is administered and somatomedin-C (SMC) levels monitored until SMC levels reach optimal levels and musculoskeletal pain and fatiguability symptoms subside.

10 Claims, 1 Drawing Sheet

THERAPEUTIC TREATMENT OF FIBROMYALGIA

FIELD OF THE INVENTION

The present invention relates to the discovery of a link between sleep anomaly-induced suboptimal secretion of growth hormone and the treatment of syndromes such as fibromyalgia which are manifested by non-restorative sleep and muscle pain.

REFERENCES

Several publications are referenced herein. disclosures of these publications are hereby incorporated herein by reference in their entirety, unless otherwise noted.

BACKGROUND OF THE INVENTION

Over the past decade there has been a growing realization that the fibromyalgia syndrome represents a very common cause of widespread musculoskeletal pain and fatiguability (A-C). According to a recent position paper by the American College of Rheumatology, fibromyalgia is now the second most common cause for rheumatology referrals after rheumatoid arthritis (D).

The pain experienced by fibromyalgia patients arises from their muscles and is activated by even minimal exertion. It has been hypothesized that the muscle pain in fibromyalgia patients is akin to the universal experience of post-exertional muscle pain (E, F)—a phenomenon which is well-known to be due to muscle microtrauma (G-J). It would appear that in fibromyalgia patients, muscle microtrauma occurs at very low levels of exertion and is much slower to heal than in normal individuals. The resulting functional disability often causes a significant curtailment in the quality of life as regards both vocational and avocational activities.

Patients with the fibromyalgia syndrome have abnormal sleep pattern characterized by EEG changes termed the alpha delta sleep anomaly (K, L). The sleep anomaly is characterized by an abnormal EEG in stages 3 and 4 of non-REM sleep with a super-imposition of a waking rhythm (10 cps—alpha rhythm) over the typical stage 4 rhythm cycles cps—delta rhythm). Furthermore, the induction of this sleep anomaly in healthy adults results in symptoms and clinical findings similar to those noted in fibromyalgia patients (M). The clinical correlative of EEG abnormality is non-restorative sleep—typically these patients awaken feeling tired and exhausted even if they have slept a normal number of hours.

Most patients with fibromyalgia have a reduced "quality of life", particularly as regards physical exertion, sleep, employment, sex life, vocational pursuits and maintaining friendships (AA). Heretofore, there has been no generally accepted efficacious treatment of fibromyalgia (F,AB); the best that could be achieved was to help patients learn to live with their problem through costly multidisciplinary treatment programs (1).

For many years the link between abnormal sleep and muscle pain remained an enigma. My discovery of low levels of somatomedin-C in a majority of patients with the fibromyalgia syndrome provides a link between sleep and muscle pain (N).

Growth hormone, through its action on the liver and the stimulation of somatomedin-C production, is an important hormone in maintaining muscle homeostasis (O, P). Recent studies attest to the beneficial effects of supplemental growth hormone in growth hormone deficient adults (Q-V).

I have discovered that fibromyalgia patients have a highly significant reduction in their somatomedin-C levels (p=0.000001). Accordingly, supplemental growth hormone injections would provide a clinical benefit in the treatment of fibromyalgia.

SUMMARY OF THE INVENTION

The present invention provides, for the first time, a specific and effective method for the treatment of fibromyalgia syndrome and other syndromes characterized by muscle pain and sleep disturbance.

Accordingly, an object of this invention is to provide a method for effective treatment of fibromyalgia and fibromyalgia-like symptoms. It is also an object of this invention to provide a pharmaceutical composition for such treatment.

Additional objects and advantages of the invention will be set forth in part in the description that follows, and in part will be obvious from the description, or may be learned by practice of the invention. The objects and advantages of the invention will be attained by means of the instrumentalities and combinations particularly pointed out in the appended claims.

To achieve the objects and accordance with the purpose of the invention, as embodied and broadly described herein, the present invention comprises a method for the treatment of fibromyalgia syndrome in a human patient, comprising administering to the patient a pharmaceutically effective amount of growth hormone for such treatment. The present invention also comprises normalizing the patient's somatomedin-C (SMC) levels through administering periodic doses of human growth hormone until the patient's SMC levels are normalized and maintaining optimal SMC levels.

The accompanying figure, which is incorporated in and constitutes a part of the specification, illustrates an aspect of the invention and, together with the description, serves to explain the principles of the invention.

DETAILED DESCRIPTION OF THE INVENTION

Figure 1:
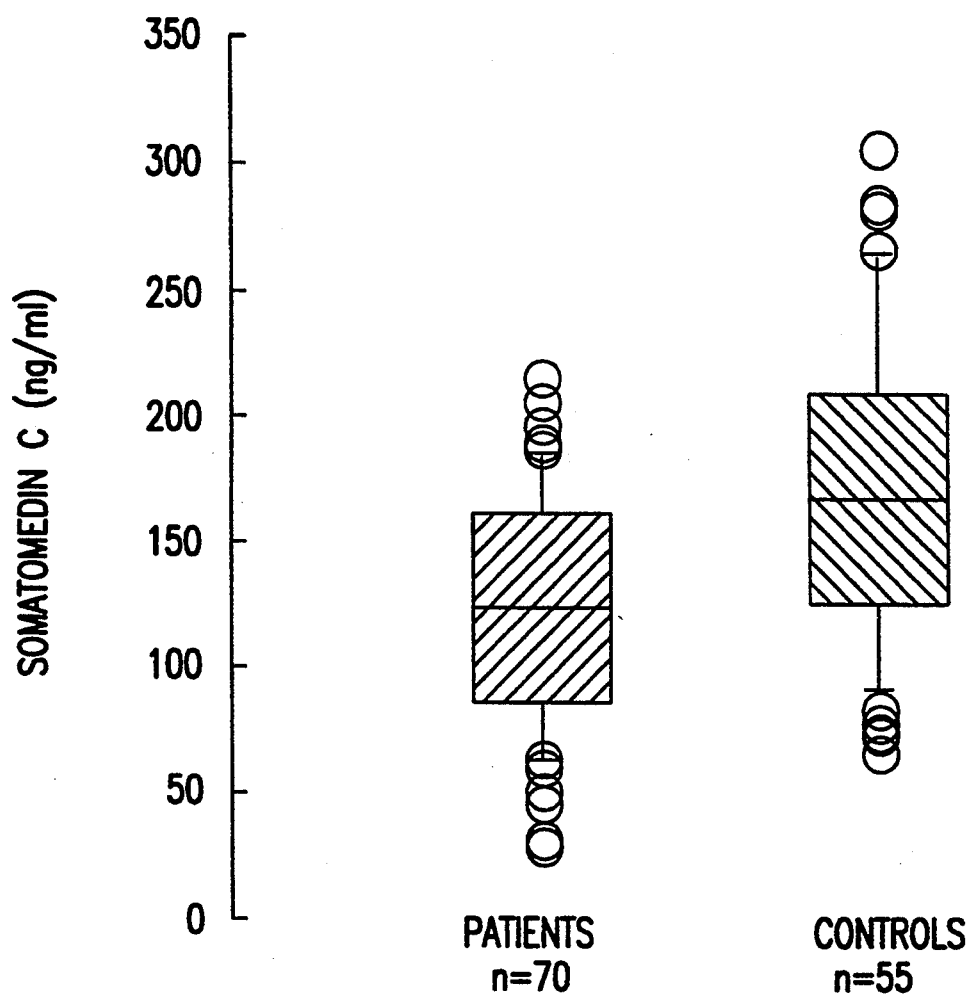
FIG. 1 depicts a box plot of data relating to somatomedin-C levels of fibromyalgia patients as compared to healthy controls. The box encompasses the 25th and 75th percentiles with a line at the mean value; the bars represent the 10th and 90th percentiles; individual dots are values outside the 10th and 90th percentiles. Patients' somatomedin-C values (mean 124.7 ng/ml±47) are significantly lower than controls (mean 175.2 ng/ml±60), P=0.000001.

Reference will now be made in detail to the presently preferred embodiments of the invention, which, together with the following example, serve to explain the principles of the invention.

The invention relates to the use of a pharmaceutically effective amount of growth hormone to treat a patient suffering from fibromyalgia-like syndromes.

The fibromyalgia syndrome is a common cause of widespread musculoskeletal pain (2). Its pathogenesis is obscure; distinctive tissue changes have not been described and laboratory investigations are usually normal. In the past the term "psychogenic rheumatism" has often been used to describe these patients on account of their confusing history of multiple somatic complaints, absence of physical findings and normal laboratory investigations. Over the last decade, rheumatologists have become increasingly aware of the large number of such patients characterized by a consistency of their history, the finding of tender areas in specific locations and absence of tenderness in other locations (3,4). In 1990 the American College of Rheumatology published guidelines for establishing a diagnosis of fibromyalgia (5).

A seminal finding in the study of fibromyalgia was provided by Moldofsky et. al. in 1975 when they described a distinctive disturbance of stage 4 sleep characterized by alpha intrusion into the normal delta rhythm (6). Induction of this sleep abnormality in healthy volunteers produced a transient syndrome similar to fibromyalgia (7). Many metabolic, endocrine and immune functions follow distinctive diurnal rhythms. Stage 4 sleep is closely related to the pulsatile secretion of growth hormone (GH); approximately 80% of the total daily production of GH is secreted during this stage of sleep (8).

Sub-optimal levels of Somatomedin-C in patients with fibromyalgia is an important factor in their apparent predisposition to muscle microtrauma. The link with abnormal sleep results from the observation that growth hormone is secreted in a pulsatile fashion mainly during stage 4 sleep (W-Y). The characteristic sleep anomaly in fibromyalgia patients leads to sub-optimal secretion of growth hormone and the resulting low levels of somatomedin-C predisposes to muscle microtrauma and impairs its healing (Z).

METHODS

Seventy female patients with the fibromyalgia syndrome were compared to 55 controls. Serum samples were obtained between 10.00 and 16.00 hours from consecutive patients attending the Oregon Health Sciences University Fibromyalgia Treatment Program. A diagnosis of fibromyalgia was made in accordance with the 1990 guidelines of the American College of Rheumatology (4). The 55 controls comprised 43 female blood donors from the Portland Red Cross and 12 female laboratory personnel. All the controls were reportedly in good health and not taking any medications. Serum somatomedin C levels were assayed by Endocrine Sciences (Calabasas Hills, Calif.) using an immunoassay employing an antiserum directed against a synthetic segment of the protein (amino acids 57-70) (9); the interassay coefficient of variation of the assay was 10%. Prior to assay, each sample was acid extracted from serum to minimize errors due to somatomedin binding proteins. Statistical analysis of the differences between fibromyalgia patients and the controls employed a Student's t-test with two tailed distribution. The contribution of age and the duration of illness to SMC levels was assessed by multiple regression analysis.

RESULTS

TABLE 1

| Demographic Characteristics of Patients and Controls | | |
| --- | --- | --- |
| | Patients (n = 70) | Controls (n = 55) |
| Sex | All female | All female |
| Age | 47.6 ± 10 | 45.6 ± 13 |
| Duration of FM | 11.6 ± 6.9 | N.A. |
| Taking HCAs | 27 | N.A. |

TABLE 1-continued

| Demographic Characteristics of Patients and Controls | | |
| --- | --- | --- |
| | Patients (n = 70) | Controls (n = 55) |
| Taking NSAIDS | 41 | N.A. |

The characteristics of the fibromyalgia patients and controls are shown in Table 1. Somatomedin-C values for both patients and controls are shown in the form of a box plot (FIG. 1); the mean SMC levels in fibromyalgia patients and controls were 124.7 ng/ml±47 and 175.2 ng/ml ±60 respectively. This difference is robustly significant according to Student's t-test (P=0.000001). Seventy-three percent and 69% of fibromyalgia patients fell below the 95% and 99% confidence limits for the mean of the control population respectively. Regression analysis indicated that age accounted for 14% of the variance in SMC levels in the control group, whereas in the fibromyalgia group age accounted for 7% of the variance. The duration of fibromyalgia accounted for less than 1% of the variance. Twenty-seven patients were taking low dosages of tricyclic anti-depressant medications to improve sleep, 43 were not; the SMC values were 129.4 ng/ml and 120.1 ng/ml respectively (P=0.54). Forty-one patients were taking NSAIDS and 29 were not; the SMC levels were 124.7 ng/ml and 121.8 ng/ml respectively (P=0.47).

DISCUSSION

A conspicuous feature of the fibromyalgia syndrome has been the absence of any reproducible pathophysiology or abnormal laboratory tests. I have discussed that, as a group, fibromyalgia patients have significantly lower serum levels of SMC than healthy controls.

Approximately 80% of GH is produced during stage 4 sleep. The alpha delta sleep anomaly, which occupies approximately 60% of stage 4 sleep in patients with fibromyalgia, disrupts the nocturnal secretion of GH. While not wishing to be bound by theory, it is believed that the low levels of SMC reported here may result from such a mechanism.

A previous study measured GH levels in fibromyalgia patients with samples taken at 0800 and 1600 hours; no differences were found between patients with fibromyalgia and rheumatoid arthritis (11). As GH only has a half life of 30 minutes, this study would not have detected reduced nocturnal secretion. Somatomedin-C has a half life of about 20 hours and its serum level is considered to reflect the integrated secretion of GH (8). The other major stimuli for GH release are: hypoglycemia, starvation, large protein meals, elevated levels of circulating amino acids, surgical trauma and other acute stresses such as exercise. A progressive diminution of regular exercise is commonly encountered in the fibromyalgia syndrome, due to post-exertional muscle pain and profound fatigue. In one study over 80% of patients with fibromyalgia were found to be anaerobically unfit, as assessed by their VO2 max when exercised to volitional exhaustion (12). A lack of regular physical exercise may also be a contributing factor to the low levels of SMC observed in some fibromyalgia patients.

Most fibromyalgia patients locate the site of their pain to muscle and typically complain of a post-exertional increase in pain. There is a large body of evidence that links post-exertional pain to muscle microtrauma (16–18) and it has been hypothesized that the musculoskeletal pain experienced in fibromyalgia has a similar origin (10). This paradigm predicts that patients with the fibromyalgia syndrome are either peculiarly susceptible to muscle microtrauma at very low levels of exertion, or are defective in the repair processes which normally lead to a resolution of muscle microtrauma (19). In fibromyalgia patients, persistent disruption of GH secretion either predisposes to muscle microtrauma and/or impairs the normal healing of muscle microtrauma, as a result of reduced anabolic stimulation from chronically low levels of SMC.

My discovery provides insight into a psycho-neuroendocrine dysfunction which is and will be useful in treatment of fibromyalgia and similar syndromes manifested by non-restorative sleep and muscle pain and in further research toward understanding the mind-body relationship if these enigmatic disorders.

This invention also relates to compositions of a therapeutically effective amount of growth hormone in admixture with a pharmaceutically acceptable carrier. Growth hormone is an anabolic peptide which stimulates increased synthesis of DNA, RNA and proteins; this effect is mediated via its stimulation of SMC secretion by the liver. In adults the GH-SMC axis has been shown to be important in muscle homeostasis (13,14); therapeutic administration of GH has recently been shown to reverse the muscle loss associated with the aging process (15).

The growth hormones of the present invention are contemplated for human uses in the form of pharmaceutical products possessing growth hormone activity. Such pharmaceutical preparations contain, as at least one of the active ingredients, human growth hormone and also appropriate, pharmaceutically acceptable carriers, diluents, fillers, binders, and other excipients depending on the dosage form contemplated. For oral administration, steps must be taken to prevent degradation in the digestive track. Enteric coated dosage forms are contemplated as one form suitable for oral administration. It is also contemplated that pharmaceutical preparations containing growth hormone can be administered locally, as by injection or topical application, intravenously, intraocularly, subconjunctively, intramuscularly, and intrathecally. The mode of administration will necessarily depend upon the ailment involved.

In another embodiment, the invention comprises a method for normalizing the SMC level and, consequently, alleviating fibromyalgia-like symptoms by administering supplemental human growth hormone to a patient suffering such symptoms. The method comprises administering an effective amount of growth hormone. Preferably, it is admixed with a pharmaceutically acceptable carrier. When administered, the pharmaceutical composition functions to increase the body's SMC level, suppressing the microtrauma response. Accordingly, the method provided by this embodiment is particularly useful in preventing pain and fatigue in disorders manifesting musculoskeletal pain and fatigue symptoms secondary to sleep disturbance, particularly where such disturbance interferes with normal stage 3 or stage 4 sleep.

The growth hormone composition of the present invention can be used to treat any disorder in which nonrestorative sleep and muscle pain play a role. For example, it can be used to treat fibromyalgia. In addition, it can be used to treat chronic fatigue syndrome. Growth hormone can also be used to control other disorders in which non-restorative sleep causes problems, such as occurs in sleep apnea and nocturnal myoclonus (periodic leg movement disorder).

In accordance with the present invention, a process is provided for treating disorders in humans manifested by non-restorative sleep and muscle pain, by administering an effective amount of human growth hormone in admixture with a pharmaceutically acceptable carrier. The disorders that may be treated include fibromyalgia syndrome and other diseases, e.g., chronic fatigue syndrome. In a preferred embodiment, a therapeutically effective amount of human growth hormone in admixture with a pharmaceutically acceptable carrier is administered subcutaneously or intramuscularly.

The amount of the growth hormone to be administered would depend upon the particular disorder being treated. Such a determination is routinely made by those of ordinary skill in the art in determining therapeutic dosages and is within the scope of tasks routinely performed by them without undue experimentation. In a preferred embodiment, the patient will be administered a periodic dose sufficient to gradually restore the normal SMC level without causing undue side effects. Preferably, the initial dose is in the range of from 0.01 to 0.06 mg per kg of body weight three times per week. The dose may be increased, until SMC levels are normalized to about 275–350 ng/ml, by increasing the dose regimen up to about four times the starting regimen.

EXAMPLE

TREATMENT OF FIBROMYALGIA BY ADMINISTERING A PHARMACEUTICALLY EFFECTIVE AMOUNT OF GROWTH HORMONE

Nutropin ® (Somatotropin for injection) would be supplied by Genentech in vials containing sterilized lyophilized powder. Each vial would contain 5 mg of Somatotropin. Excipients would be mannitol, glycerin, USP for isotonicity, and phosphate for pH balance. The vial contents would be reconstituted only with bacteriostatic water for injection, USP (benzyl alcohol preserved).

Nutropin (Somatotropin for injection) would be given to the patient in an initial dose of 0.0125 mg/kg/day by subcutaneous injection for the first month. This relatively low initial dose is designed to minimize the development of side effects. The dose is increased at monthly increments to achieve a somatomedin-C level in the range of 275–350 ng/ml. If side effects such as edema, arthralgia or increased BP occur, the dose would be reduced to 0.0125 mg/kg/day until the problem subsides.

For most patients, symptoms would subside as the SMC levels reach normal levels for that patient's height/weight and age. SMC levels are then monitored and an optimal level is maintained.

REFERENCES

A. Goldenberg, D. L., Fibromyalgia Syndrome. An Emerging But Controversial Condition, *JAMA* 257:2782–2787, 1987.

B. Bennett, R. M., Fibrositis (Editorial), *JAMA* 257:2802–2803, 1987.

C. Bennett, R. M., The Fibromyalgia Syndrome, *Rheum. Dis. Clin. North Am.* 15:1–191, 1989.

Marder, W. D., Meenan R. F., Felson, D. T., Reichlin, M., Birnbaum, N. S., Croft, J. D., Dore, R. K., Kaplan, H., Kaufman, R. L., Stobo, J. D., Editorial: The Present and Future Adequacy of Rheumatology Manpower: A Study of Health Care Needs and Physician Supply, Arth. Rheum. 34:1209-1217, 1991.

E. Bennett, R. M., Etiology of the Fibromyalgia Syndrome: A Contemporary Hypothesis, Internal Medicine for the Specialist 11:48-61, 1990.

F. Bennett, R. M., Beyond Fibromyalgia: Ideas on Etiology and Treatment, J. Rheumatol. Suppl. 19:185-191, 1989.

Edwards, R. H. T., Hypotheses of Peripheral and Central Mechanisms Underlying Occupational Muscle Pain and Injury, Eur. J. Appl. Physiol. 57:275-281, 1988.

H. Newham, D. J., Mills, K. R., Quigley, B. M., Edwards, R. H., Pain and Fatigue After Concentric and Eccentric Muscle Contractions, Clin. Sci. 64:55-62, 1983.

I. Friden, J., Kjorell, U., Thornell, L. E., Delayed Muscle Soreness and Cytoskeletal Alterations: An Immunocytological Study in Man, Int. J. Sports Med. 5:15-18, 1984.

J. Friden, J., Sjostrom, M., Ekblom, B., A Morphological Study of Delayed Muscle Soreness, Experientia 37:506-507, 1981.

K. Moldofsky, H., Scarisbrick, P., England, R., Smythe, H., Musculoskeletal Symptoms and Non-REM Sleep Disturbance in Patients with "Fibrositis Syndrome" and Healthy Subjects, Psychosom. Med. 37:341-351, 1975.

L. Moldofsky, H., Sleep and Fibrositis Syndrome, Rheum. Dis. Clin. North Am. 15:91-103, 1989.

M. Moldofsky, H., Scarisbrick, P., Induction of Neurasthenic Musculoskeletal Pain Syndrome By Selective Sleep Stage Deprivation, Psychosom. Med. 38:35-44, 1976.

N. Bennett, R. M., Clark, S. R., Campbell, S. M., Burckhardt, C. S., Somatomedin-C Levels in patients with the Fibromyalgia Syndrome: A possible Link Between Sleep and Muscle Pain, Arth. Rheums, in press, 1992.

O. Fryburg, D. A., Louard, R. J., Gerow, K. E., Gelfand, R. A., Barrett, E. J., Growth Hormone Stimulates Skeletal Muscle protein Synthesis and Antagonizes Insulin's Antiproteolytic Action in Humans, Diabetes 41:424-429, 1992.

P. Rutherford, O. M., Jones, D. A., Round, J. M., Buchanan, C. R., preece, M. A., Changes in Skeletal Muscle and Body Composition After Discontinuation of Growth Hormone Treatment in Growth Hormone Deficient Young Adults, (i Clin. Endocrinol. (Oxf) 34:469-475, 1991.

Q. Vaisman, N., Zadik, Z., Shamai, Y., Franklin, L., Dukhan, R., Changes in Body Composition of patients With Subnormal Spontaneous Secretion of Growth Hormone, During the First Year of Treatment with Growth Hormone, Metabolism 41:483-486, 1992.

R. Yarssheski, K. E., Campbell, J. A., Smith, K., Rennie, M. J., Holloszy, J. O., Bier, D. M., Effect of Growth Hormone and Resistance Exercise on Muscle Growth in Young Men., Am. J. Physiol. Endocrinol. Metab. 262:E261-E267, 1992.

S. Crist, D. M., Peake, G. T., Loftfield, R. B., Kraner, J. C., Egan, P. A., Supplemental Growth Hormone Alters Body Composition, Muscle Protein Metabolism and Serum Lipids in Fit Adults: Characterization of Dose-Dependent and Response-Recovery Effects, Mech. Ageing Dev. 58:191-205, 1991.

T. Jorgensen, J. O. L., Human Growth Hormone Replacement Therapy, Pharmaceutical and Clinical Aspects, Endocr. Rev. 12:189-207, 1991.

Lundeberg, S., Belfrage, M., Wernerman, J., Von der Decken, A., Thunell, S., Vinnars, E., Growth Hormone Improves Muscle Protein Metabolism and Whole Body Nitrogen Economy in Man During a Hyponitrogenous Diet, Metabolism 40:315-322, 1991.

V. Rudman, D., Feller, A. G., Nagraj, H. S., et. al., Effects of Human Growth Hormone in Men Over 60 Years Old, N. Engl. J. Med. 323:1-5, 1990.

W. Holl, R. W., Hartman, M. L., Veldhuis, J. D., Taylor, W. M., Thorner, M. O., Thirty-Second Sampling of Plasma Growth Hormone in Man: Correlation with Sleep Stages, J. Clin. Endocrinol. Metab. 72:854-861, 1991.

X. Holl, R. W, Hartman, M. L., Veldhuis, J. D., Taylor, W. M., Thorner, M. O., Thirty-Second Sampling of Plasma Growth Hormone in Man: Correlation With Sleep Stages, J. Clin. Endocrinol. Metab. 72:854-861, 1991.

Y. Van Coevorden, A., Mockel, J., Laurent, E., Kerkhofs, M., L'Hermite-Balriaux, M., Decoster, C., Nave, P., Van Cauter, E., Neuroendocrine Rhythms and Sleep in Aging Men, Am. J. Physiol. Endocrinol. 260:E651-E661, 1991.

Z. Jensen, L. T., Jacobsen, S., Hrsley Petersen, K., Serum Procollagen Type III Aminoterminal Peptide in Primary Fibromyalgia (Fibrositis Syndrome) [letter], Br. J. Rheumatol. 27:496, 1988.

AA. Burckhardt C. S., Clark, S. R., Bennett, R. M.: The impact of fibromyalgia on the quality of life: a comparative analysis. J. Rheumatol (in press): 1992.

AB. Wolfe, F.: Fibromayalgia: whither treatment? [see comments]. J. Rheumatol 15:1047-1049, 1988.

1. Bennett, R. M., Campbell, S., Burckhardt, C., Clark, S. R., O'Reilly, C., Wiens, A.: A multidisciplinary approach to fibromyalgia treatment. J. Musculoskel Med. 8:21-32, 1991.

2. Goldenberg, D. L., Fibromyalgia Syndrome. An Emerging But Controversial Condition, JAMA 7:2782-2787, 1987.

3. Yunus, M., Masi, A. T., Calabro, J. J., Miller, K. A., Feigenbaum, S. L., Primary Fibromyalgia (Fibrositis): Clinical Study of 50 patients With Matched Normal Controls, Semin. Arthritis Rheum. 1:151-171, 1981.

4. Campbell, S. M., Clark, S., Tindall, E. A., Forehand, M. E., Bennett, R. M., Clinical Characteristics of Fibrositis. I. A "Blinded,: Controlled Study of Symptoms and Tender Points, Arthritis Rheum. 26:817-824, 1983.

5. Wolfe, F., Symthe, H. A., Yunus, M. B., Bennett, R. M., Bombardier, C., Goldenberg, D. L., Tugwell, P., Campbell, S. M., Abeles, M., Clark, P., Fam, A. G., Farber, S. J., Fiechtner, J. J., Franklin, C. M., Gatter, R. A., Hamaty, D., Lessard, J., Lichtbroun, A. S., Masi, A. T., McCain, G. A., Reynolds, E., Romano, T. J., Russell, U., Sheon, R. P., The American College of Rheumatology 1990 Criteria for the Classification of Fibromyaigia: Criteria Report of the Multicenter Criteria Committee, Arthritis Rheum. 33:160-172, 1990.

6. Moldofsky, H. J., Scarisbrick, P., England, R., Smythe, H., Musculoskeletal symptoms and Non-REM Sleep Disturbance in Patients with "Fibrositis Syndrome" and Health Subjects, Psychosom. Med. 37:341-351, 1975.

7. Moldofsky, H., Scarisbrick, P., Induction of Neurasthenic Musculoskeletal Pain Syndrome By Selective Sleep Stage Deprivation, *Psychosom. Med.* 38:35–44, 1976.

8. Florini, J. R., Prinz, P. N., Vitiello, M. L., Somatomedin-C Levels in Healthy Young and Old Men: Relationship to Peak and 24-Hour Integrated Levels of Growth Hormone, *J. Gerontol.* 40:2–7, 1985.

9. Hintz, R. L., Liu, F., Chang, D., Seegan, G., A Sensitive Radioimmunoassay for Somatomedin-C Insulin-like Growth Factor I. Based on Synthetic Insulin-like Growth Factor 57–70. *Horm. Metab. Res.* 20:344–347, 1988.

10. Bennett, R. M., Beyond Fibromyalgia: Ideas on Etiology and Treatment, *J. Rheumatol. Suppl.* 19:185–191, 1989.

11. McCain, G. A., Tilbe, K. S., Diurnal Hormone Variation in Fibromyalgia Syndrome: A Comparison with Rheumatoid Arthritis, *J. Rheumatol. Suppl.* 19:154–157, 1989.

12. Bennett, R. M., Clark, S. R., Goldberg, L., Nelson, D., Bonafede, R. P., Porter, J., Specht, D., Aerobic Fitness in Patients with Fibrositis. A Controlled Study of Respiratory Gas Exchange and 133xenon Clearance From Exercising Muscle, *Arthritis Rheum.* 32:454–460, 1989.

13. Cuneo, R. C., Salomon, F., Wiles, C. M., Hesp, R., Sonksen, P. H., Growth Hormone Treatment in Growth Hormone-Deficient Adults. II. Effects on Exercise Performance, *J. Appl. Physiol.* 70:695–700, 1991.

14. Crist, D. M., Peake, G. T., Loftfield, R. B., Kraner, J. C., Egan, P. A., Supplemental Growth Hormone Alters Body Composition, Muscle Protein Metabolism and Serum Lipids in Fit Adults: Characterization of Dose-Dependent and Response-Recovery Effects, *Mechanisms of Ageing and Development* 58:191–205, 1991.

15. Rudman, D., Feller, A. G., Nagraj, H. S., et. al., Effects of Human Growth Hormone in Men Over 60 Years Old, *N. Engl. J. Med.* 323:1–5, 1990.

16. Edwards, R. H. T., Hypotheses of Peripheral and Central Mechanisms Underlying Occupational Muscle Pain and Injury, *Eur. J. Appl. Physiol.* 57:275–281, 1988.

17. Newham, D. J., McPhail, G., Mills, K. R., Edwards, R. H., Ultrastructural Changes After Concentric and Eccentric Contractions of Human Muscle, *J. Neurol. Sci.* 61:109–122, 1983.

18. Newham, D. J., Jones, D. A., Tolfree, S. E., Edwards, R. H., Skeletal Muscle Damage: A Study of Isotope Uptake, Enzyme Efflux and Pain After Stepping, *Eur. J. Appl. Physiol.* 55:106–112, 1986.

19. Bennett, R. M., Etiology of the Fibromyalgia Syndrome: A Contemporary Hypothesis, *Internal Medicine for the Specialist* 11:48–61, 1990.

I claim:

1. A method for treatment of syndromes manifested in a human patient by non-restorative sleep and musculoskeletal pain comprising administering to said patient a pharmaceutically effective amount of human growth hormone.

2. The method of claim 1 wherein said syndrome is fibromyalgia syndrome.

3. The method of claim 1 wherein said syndrome is chronic fatigue syndrome.

4. The method of claim 1 wherein said nonrestorative sleep is characterized by the alpha delta sleep anomaly.

5. The method of claim 1 wherein said growth hormone is in a pharmaceutically acceptable carrier.

6. The method of claim 1 wherein said growth hormone is administered subcutaneously or intramuscularly.

7. The method of claim 6 wherein said growth hormone is administered in a dosage in the range of 0.01 to 0.06 mg/kg body weight.

8. The method of claim 7 wherein said dosage is administered three times per week.

9. The method of claim 7 wherein said growth hormone is administered in a range of from 0.01 to 0.06 mg/kg body weight three times per week and the dosage is then gradually increased until said patient has optimal somatomedin-C levels.

10. The method of claim 9 wherein said dosage us gradually increased up to the range of from 0.04 to 0.24 mg/kg,24 mg/kg body weight.

* * * * *